(12) United States Patent
Smits et al.

(10) Patent No.: US 6,620,100 B2
(45) Date of Patent: Sep. 16, 2003

(54) HEARING EVALUATION DEVICE WITH NOISE-WEIGHTING CAPABILITIES

(75) Inventors: Matthijs P. Smits, Sherwood, OR (US); Aaron R. Thornton, West Des Moines, IA (US)

(73) Assignee: Natus Medical Inc., San Carlos, CA (US)

( * ) Notice: Subject to any disclaimer, the term of this patent is extended or adjusted under 35 U.S.C. 154(b) by 14 days.

(21) Appl. No.: 09/982,321

(22) Filed: Oct. 17, 2001

(65) Prior Publication Data

US 2003/0073920 A1 Apr. 17, 2003

(51) Int. Cl.[7] .................................................. A61B 5/00
(52) U.S. Cl. ........................ 600/300; 600/544; 600/559
(58) Field of Search ................................ 600/300, 559, 600/544

(56) References Cited

U.S. PATENT DOCUMENTS

| | | | | |
|---|---|---|---|---|
| 5,003,986 A | * | 4/1991 | Finitzo et al. ............... | 600/544 |
| 5,601,091 A | * | 2/1997 | Dolphin et al. ............. | 600/544 |
| 6,196,977 B1 | * | 3/2001 | Sininger et al. ............ | 600/559 |
| 6,200,273 B1 | * | 3/2001 | Sininger et al. ............ | 600/559 |
| 6,264,616 B1 | * | 7/2001 | Don ........................... | 600/559 |
| 6,343,230 B1 | * | 1/2002 | Smits et al. ................. | 600/544 |
| 6,475,163 B1 | * | 11/2002 | Smits et al. ................. | 600/559 |
| 6,556,861 B1 | * | 4/2003 | Prichep ....................... | 600/544 |

OTHER PUBLICATIONS

Elberling & Wahlgreen, *Estimation of Auditory Brainstem Response, ABR, By Means of Bayesian Inference*, Scand. Audiol. vol. 14: pp. 89–96 (1985).

Don & Elberling, *Evaluating Residual Background Noise in Human Auditory Brain–Stem Responses*, J. Acoust. Soc. Am. vol. 96 (5), pp. 2746–2757 (Nov. 1994).

Lutkenhoner, Hoke, and Pantev, *Possibilities and Limitations of Weighted Averaging*, Biol. Cybernetics. vol. 52, pp. 409–416, (Spring 1985).

John, Dimitrijevic, & Picton, *Weighted Averaging of Steady State Responses*, Clinical Neurophysiology, vol. 112, pp. 555–562, (2001).

\* cited by examiner

Primary Examiner—Robert L. Nasser
(74) Attorney, Agent, or Firm—Daniel P. Maguire (57) ABSTRACT

An apparatus and method for evaluation of hearing loss is disclosed. The apparatus and method use evoked Auditory Brainstem Responses (ABR) to determine if the subject is able to hear repeatedly administered click stimuli. In order to optimize evaluation, the present invention uses normative data to accurately weight the auditory responses, so that evaluation will be possible in different or changing noise conditions.

45 Claims, 4 Drawing Sheets

Fig. 4 ial noises.

HEARING EVALUATION DEVICE WITH NOISE-WEIGHTING CAPABILITIES

RELATED APPLICATIONS

This application is related to the co-pending and commonly assigned U.S. Patent Application entitled "Hearing Evaluation Device with Patient Connection Evaluation Capabilities," application Ser. No. 09/479,559, filed by Matthijs P. Smits, Vineet Bansal, Abraham J. Totah and Bryan P. Flaherty and the U.S. Patent Application entitled "Hearing Evaluation with Noise Detection and Evaluation Capability," application Ser. No. 09/479,548 filed by Matthijs P. Smits and Bryan P. Flaherty and the U.S. Patent Application entitled "Hearing Evaluation with Predictive Capabilities," application Ser. No. 09/479,557, filed by Matthijs P. Smits and Christophe M. Coppin, the disclosures of which are hereby incorporated herein by reference.

1. FIELD OF THE INVENTION

The present invention relates to devices and methods that use electroencephalographic responses to auditory stimuli to evaluate the hearing of a subject, and that are capable of weighting the response to an auditory stimulus based upon an analysis with normative data.

2. BACKGROUND OF THE INVENTION

In the past, hearing impairment in babies and children was often not detected until after it was observed that the baby or child did not respond normally to sound. Unfortunately, it often took months or even years for the parent to observe the impairment, and by that time the child's language and learning abilities were negatively and often irreversibly impacted. Indeed, recent studies indicate that the vocabulary skills of hearing impaired children markedly increase if their hearing loss is detected early. The optimal time to evaluate hearing loss is thus immediately after birth, both because early detection allows for early treatment, and because parents often fail to bring their infants to later appointments. As a result, a number of states have implemented programs to evaluate newborns for hearing loss.

However, babies, especially newborns, cannot participate in traditional hearing tests, which require the subject to indicate if he or she hears the auditory stimulus. Thus, devices and methods have been developed to objectively determine hearing loss, without the voluntary participation of the subject. One such method involves analyzing the involuntary electroencephalographic (EEG) signals evoked from a subject in response to an auditory stimulus. When a subject perceives a sound having particular characteristics, a specific EEG waveform known as an Auditory Brainstem Response (ABR) is generated. This ABR response signal is typically small in magnitude in relation to general EEG activity. Therefore, statistical and signal processing techniques have been employed and developed to help detect, to a pre-defined level of statistical confidence, whether an ABR response has in fact been evoked. ABR testing is especially applicable to evaluation of infants, but can be applied to any subject.

The ABR that is evoked in response to the auditory stimulus may be measured by use of surface electrodes on the scalp or neck. As a practical matter, the electrodes will also detect noise signals from neural activity (besides the ABR), muscle activity, and non-physiological environmental noises.

Typically, ABR testing becomes more difficult and time consuming with higher levels of noise, because noise obscures the evoked auditory response. Therefore, when conducting ABR testing, it is important to measure noise, and to control for the effects of such noise. The present invention provides for an improved method to optimize ABR hearing testing to account for the effects of noise. The improved method, which uses normative data, can shorten testing time and improve accuracy, thereby making such tests more attractive to parents and health care providers.

3. DESCRIPTION OF THE PRIOR ART

Several techniques have been used to minimize the physiological noise in the EEG response from an auditory stimulus (see M. Don and C. Elberling, *Evaluating Residual Background Noise in Human Auditory Brain—Stem Responses*, J. Acoust. Soc. Am. 96 (5), Pt. 1: 2746–2757 (1994)), including signal averaging and weighted signal averaging, signal filtering, artifact rejection, stimulus modification, targeted electrode placement, and various techniques designed to relax or sedate the subject.

The prior art details weighting techniques that evaluate the noise content in an EEG response and apply weights relative to the noise content of other EEG responses (see C. Elberling and O. Wahlgreen, *Estimation of Auditory Brainstem Response, ABR, By Means Of Bayesian Inference*, Scand. Audiol., 14:89–96, (1985); M. Hoke, B. Ross, R. Wickesberg, and B. Lutkenhoner, *Weighted averaging—Theory and application to electric response audiometry*, Electroencephalogr. Clin. Neurophysiol., 57, 484–489 (1984); B. Lutkenhoner, M. Hoke, and C. Pantev, *Possibilities and limitations of weighted averaging*, Biol. Cybernet., 52, 409–416, (1985)). However, this prior art does not provide for weighting that is anchored to an absolute minimum expected ABR amplitude based on normative data. In addition, prior art does not describe weighting the EEG response relative to one or more characteristics of ambient acoustic noise at the time of the auditory stimulus. Additionally, the prior art does not reveal or suggest the use of noise weighting in conjunction with signal analysis that transforms the EEG response into a series of polarities to determine the probability of the presence of an ABR response.

///
///

4. OBJECTS AND SUMMARY OF THE INVENTION

The present invention provides a device and method for use in analyzing the EEG signal evoked in response to the auditory click stimulus, to determine if the subject suffers from hearing loss. Broadly, the invention is directed to devices and methods that are capable of weighting the response to an auditory stimulus based upon an analysis with normative data.

In one embodiment of the invention, evoked EEG responses to auditory stimuli are collected, and organized into "sweeps," with each sweep containing the response signal for one auditory stimulus. The sweeps are organized into C blocks, with each block c containing a number of sweeps $N_c$. The noise content of each block c is determined and compared with the allowable noise content associated with the absolute minimum expected ABR amplitude, from which an associated weight $w_c$ is calculated.

The response signal for each sweep is digitized and converted into a series of binary numbers (0 or 1) corresponding to whether the amplitude of the response signal is positive or negative at various points in time. The digitized, binary waveform is compared to a benchmark ABR waveform to determine if the ABR is present. To make this determination, a polarity sum is calculated, which represents the sum of the polarities of the response signals within a block at each measured point in time. The polarity sum of each block is multiplied with the associated weight, and combined into a polarity sum for all weighted blocks. Statistical techniques are then used to determine if an ABR is present, relying upon the expected distribution of polarity sums in the absence of an ABR. This expected distribution is developed theoretically. A "Pass" is triggered if the observed polarity distribution, as represented in a specifically defined test statistic, indicates that the likelihood that an ABR is present is above a predetermined statistical threshold. After a certain number of blocks have been completed, evaluation will cease if a "Pass" has yet not been triggered. Under such circumstances, the subject will be referred for further testing to determine if he or she in fact does suffer from hearing loss.

In accordance with the present invention, the polarity sum for each block is weighted based on its noise content in comparison with normative data for a hearing subject. These normative data reflect the maximum allowable noise content that would still permit testing for a hearing subject with a very weak ABR waveform. The present invention improves upon the prior art because it provides an accurate way to compensate for different or changing noise contents, therefore conserving evaluation times and resources, without sacrificing evaluation accuracy.

Although the embodiments described here are directed towards evaluation of newborn hearing, it is believed that the present invention can be applied to any evaluation, whether of hearing or not, in which evoked potentials are analyzed.

As described below, the present invention makes extensive use of normative data. These normative data were derived from analysis of clinical data, and from computer simulations representing different testing conditions. The normative data employed in the preferred embodiment of the present invention are reflected in the drawings described in the subsequent paragraph.

5. BRIEF DESCRIPTION OF THE DRAWINGS

Further features, elements, and advantages of the present invention will become apparent to a person of ordinary skill in the art in view of the following detailed description of a preferred embodiment of the present invention, made with reference to the drawings annexed, in which like reference characters correspond to like elements, and in which.

6. DESCRIPTION OF THE PREFERRED EMBODIMENT a. Overview

The invention disclosed herein detects, processes and analyzes the EEG response of a subject to certain sound stimuli. A click sound stimulus is repetitively applied to the subject's ear through a transducer. The click stimuli may be applied to one ear at a time (monoaurally), or to both ears simultaneously (binaurally). In a preferred embodiment, monoaural stimuli are applied at 37 Hz.

The EEG response is detected from surface electrodes. Testing may be performed to ensure that the electrodes have been properly placed, and that nothing is impeding the electrodes' ability to detect the EEG response signal. (See U.S. Patent Application entitled "Hearing Evaluation Device With Patient Connection Evaluation Capabilities").

Figure 3:
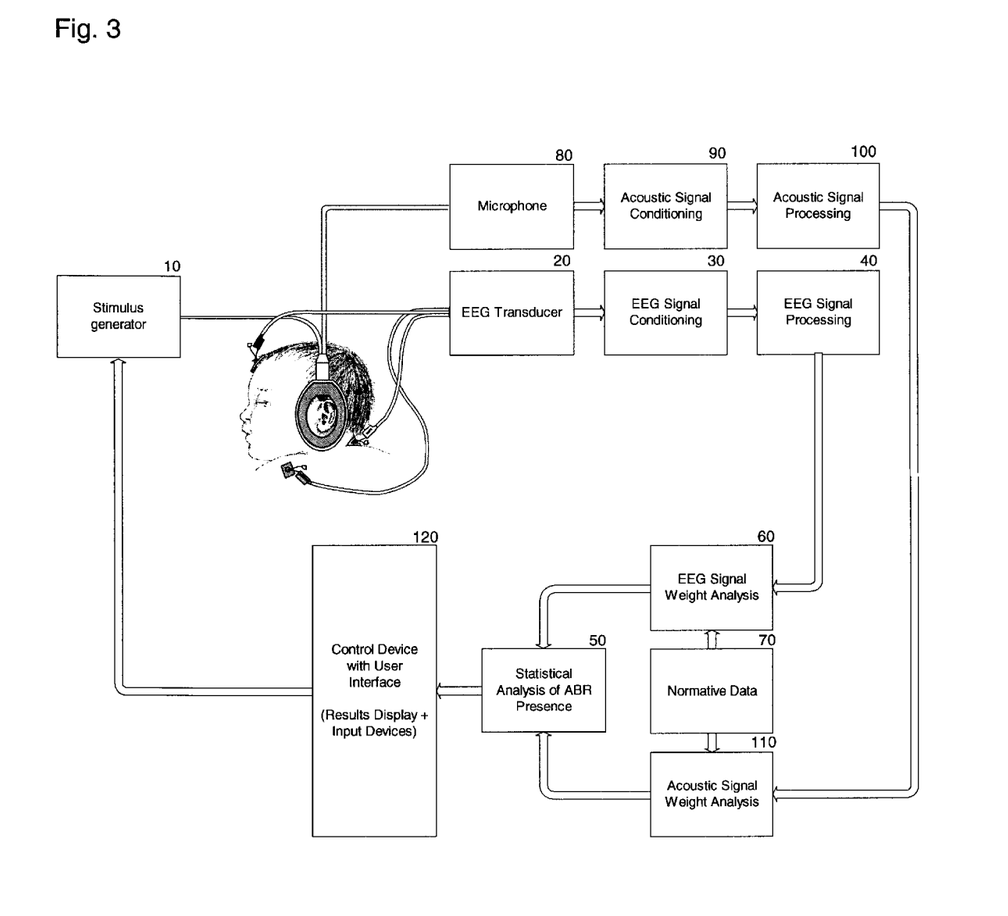
FIG. 3 is a block diagram of the components of the testing apparatus of the present invention.

In a preferred embodiment, the electrodes are placed on the subject in the following manner: a positive electrode is placed on the forehead, a negative electrode is placed on the nape of the neck, and a ground electrode is placed on the mastoid or shoulder (FIG. 3). The EEG signal detected from these electrodes is filtered so as to exclude signals that are not applicable to the ABR.

The amplitude of the EEG response is digitized, and is assigned a binary value (0 or 1). This binary value represents the amplitude polarity of the waveform, that is, whether the EEG amplitude is positive (1) or negative (0), at the measured time.

The stimuli and responses are grouped into "sweeps" and "blocks." A sweep is a response waveform to a single click stimulus. A block is a series of sweeps, and in a preferred embodiment, represents 10 accepted click stimulus responses. We refer to "accepted" click stimulus responses, because some sweeps may be rejected due to problems with the testing conditions. (See U.S. Patent Application entitled "Hearing Evaluation Device With Noise Detection and Evaluation Capability").

Upon completion of a block of accepted sweeps, signal averaging is used to compute the composite waveform that results from this block. In addition, signal variance is calculated to estimate the noise content of this block. This variance is compared with a maximum allowable variance for an absolute minimum expected ABR amplitude, whose ratio defines a weight, which is multiplied with the composite waveform. In turn, signal averaging is used again to compute the average weighted composite waveform from all blocks. This average weighted composite waveform is then compared with an internal template, to determine if the null hypothesis ($H_0$) can be rejected. The null hypothesis is the hypothesis that there is no ABR, and will be rejected if the probability of an ABR being present is above a certain pre-set statistical threshold. In the preferred embodiment, the null hypothesis is rejected, and the evaluation ceases, when sufficient data have been collected to conclude, with 99.96% statistical confidence, that an ABR waveform is present. A "Pass" or other similar message may then be generated.

If the average weighted composite waveform is insufficient to reject the null hypothesis, then the evaluation continues until the sum of the weights of all blocks exceeds a preset threshold. In a preferred embodiment, the threshold is 15,000 weighted sweeps.

/ / / b. Signal Analysis

The chief challenge in using ABR to evaluate hearing loss is the difficulty in detecting the ABR response (if any) from the noise within which it is buried. This noise is typically Gaussian-distributed, with a mean amplitude of zero, and with changing variance.

As stated above, the present invention detects the presence of an ABR by repetitively applying click stimuli in blocks c of $N_c$=10 sweeps. Each click stimulus is comprised of a brief acoustic pulse primarily composed of frequencies in the 500–4000 Hz range. The repetition rate for the clicks is 37 Hz. The polarities of the click stimuli are sequentially alternated between condensation (positive square pulse) and rarefaction (negative square pulse) stimuli. Since the noise typically has a mean of zero and no component is synchronous with the stimulus repetition rates, it is likely to sum toward zero with increasing sweeps, leaving the ABR.

Under the preferred embodiment of the present invention, the amplitude sequence of each click stimulus response is converted into a sequence of polarities (positive or negative), which, in turn, is summed with the other response polarity sequences in block c, to form the array $X_c$. For instance, an amplitude sample in the click stimulus response would be given a "1" if this amplitude were positive (no matter how high), and a "0" if this amplitude were negative (no matter how low). And, if no ABR were present the expected proportion of polarities would be 0.5. However, if an ABR were present, the proportion would likely be higher. The proportion of polarities in an evoked response matching the ABR waveform is related to the amount of signal noise.

/ / /
/ / /
/ / /

After each block of sweeps, the signal variance $\sigma_c^2$ for block c is calculated, as defined by:

$$\begin{cases} \sigma_c^2 = \dfrac{\sum_{n=1}^{N_C} \sum_{t=1}^{T} (s_n(t) - \mu_c)^2}{N_c T - 1} \\ \mu_c = \dfrac{\sum_{n=1}^{N_C} \sum_{t=1}^{T} s_n(t)}{N_c T} \end{cases}$$

In turn, a weight $w_c$ is determined based on the ratio between the signal variance $\sigma_c^2$ and a maximum allowable variance for a minimum expected ABR waveform ($5^{th}$ percentile), following:

$$\begin{cases} w_c = \dfrac{\sigma_{\min}^2}{\sigma_c^2} & \text{for } \sigma_c^2 \geq \sigma_{\min}^2 \\ w_c = 1 & \text{for } \sigma_c^2 < \sigma_{\min}^2 \end{cases}$$

In a preferred embodiment of the present invention, the maximum allowable variance, $\sigma_{min}^2$, is $1.7 \times 10^{-11}$ Volts$^2$. This value represents the variance level at which, on average, the hearing test passes without weighting for a subject whose ABR waveform is in the bottom $5^{th}$ percentile of all ABR waveforms in terms of amplitude.

Figure 4:
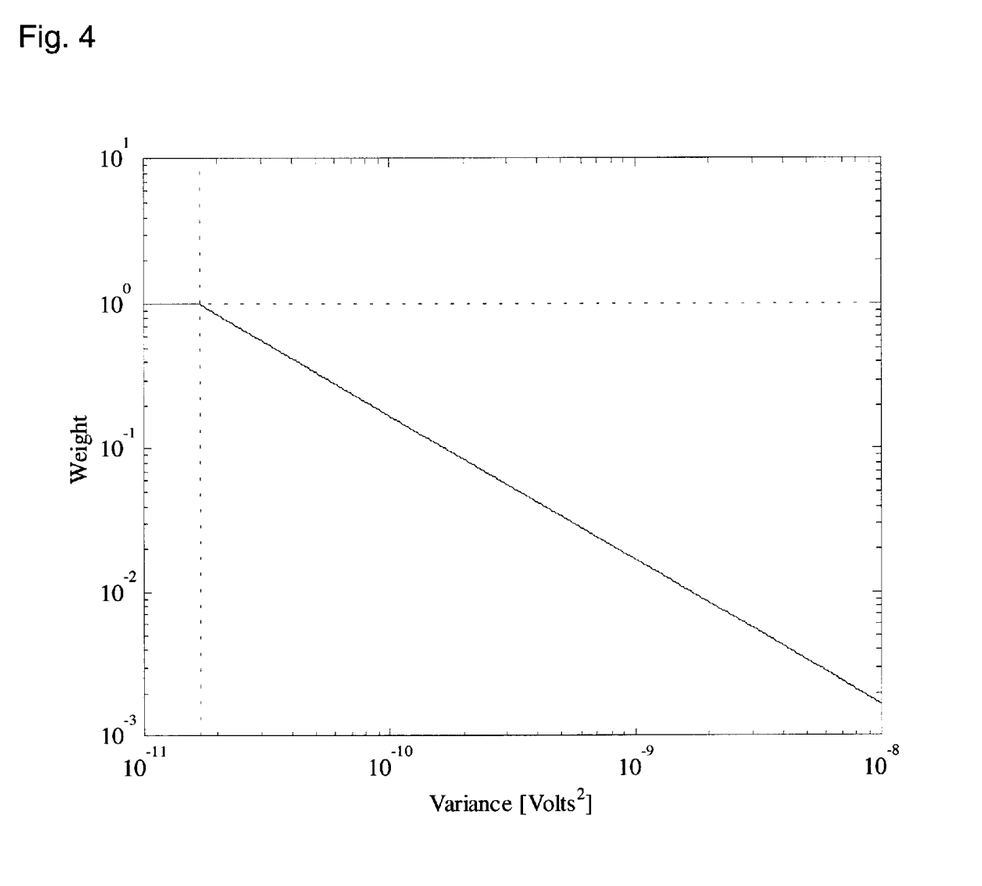
FIG. 4 illustrates the weight as a function of noise variance for a $5^{th}$ percentile ABR waveform.

The relationship between the assigned weights and the variance is provided in FIG. 4. As illustrated in that figure, the weight can never exceed 1, regardless of how little noise is present. Additionally, a lower limit could also be used, so that any sweep with a weight below a preset threshold is assigned a weight of 0, and therefore not used at all.

The present invention assigns weights based on the continuous relationship between the variance and the normative data. By continuous relationship, we are referring to the fact that there are an infinite or very high number of weights that can be assigned, as opposed to a step relationship, under which a number of "bins" or categories of weights are used. For purposes of this patent, "continuous relationship" refers to any system that can assign 50 or more weights.

Now, the summed polarity sequence $X_c$ for block c is multiplied with the associated weight $w_c$ and summed with the other summed polarity sequences into an array X. Also, the total weighted number of sweeps N is calculated as the sum of the number of sweeps multiplied by the square of the respective weights in each block:

$$\begin{cases} X = \sum_{c=1}^{C} X_c w_c = \sum_{c=1}^{C} \left[ \sum_{n=1}^{N_c} X_n \right] w_c \\ N = \sum_{c=1}^{C} N_c w_c^2 \end{cases}$$

EEG signal noise weighting could also be conducted with other parameters besides variance, such as standard deviation, higher moments of the signal distribution, frequency, zero crossings, or other descriptions of the signal.

In addition to weighted averaging with respect to the EEG signal noise, a similar technique can be devised for acoustic noise. Besides obscuring the evoked EEG response, acoustic noise can also directly degrade the ABR waveform, because it can mask the aural stimulus, thereby preventing or hindering the formation of the ABR response. To counteract these effects, each sweep can also be weighted with respect to its acoustic noise level, which can be determined by evaluation of signal energy E (See U.S. Patent Application entitled "Hearing Evaluation Device With Noise Detection and Evaluation Capability"). Then, an additional weighting $w_n$ can be determined for each sweep based upon the degradation of the ABR waveform with acoustic noise levels:

$$\begin{cases} w_n = \dfrac{E_{\min}}{E} & \text{for } E \geq E_{\min} \\ w_n = 1 & \text{for } E < E_{\min} \end{cases}$$

The $E_{min}$ value represents the minimum level of acoustic noise that causes significant degradation of the ABR. It can be calculated by providing controlled levels of acoustic noise with the click stimuli, followed by visual inspection of the resultant ABR waveforms. The lowest level of acoustic noise that causes ABR degradation is then identified as $E_{min}$. Together with the EEG noise-weighted averaging, the noise-weighted algorithm can now be expanded to:

$$\begin{cases} X = \sum_{c=1}^{C} X_c w_c = \sum_{c=1}^{C} \left[ \sum_{n=1}^{N_c} X_n w_n \right] w_c \\ N = \sum_{c=1}^{C} \left[ \sum_{n=1}^{N_c} w_n^2 \right] w_c^2 \end{cases}$$

Figure 1:
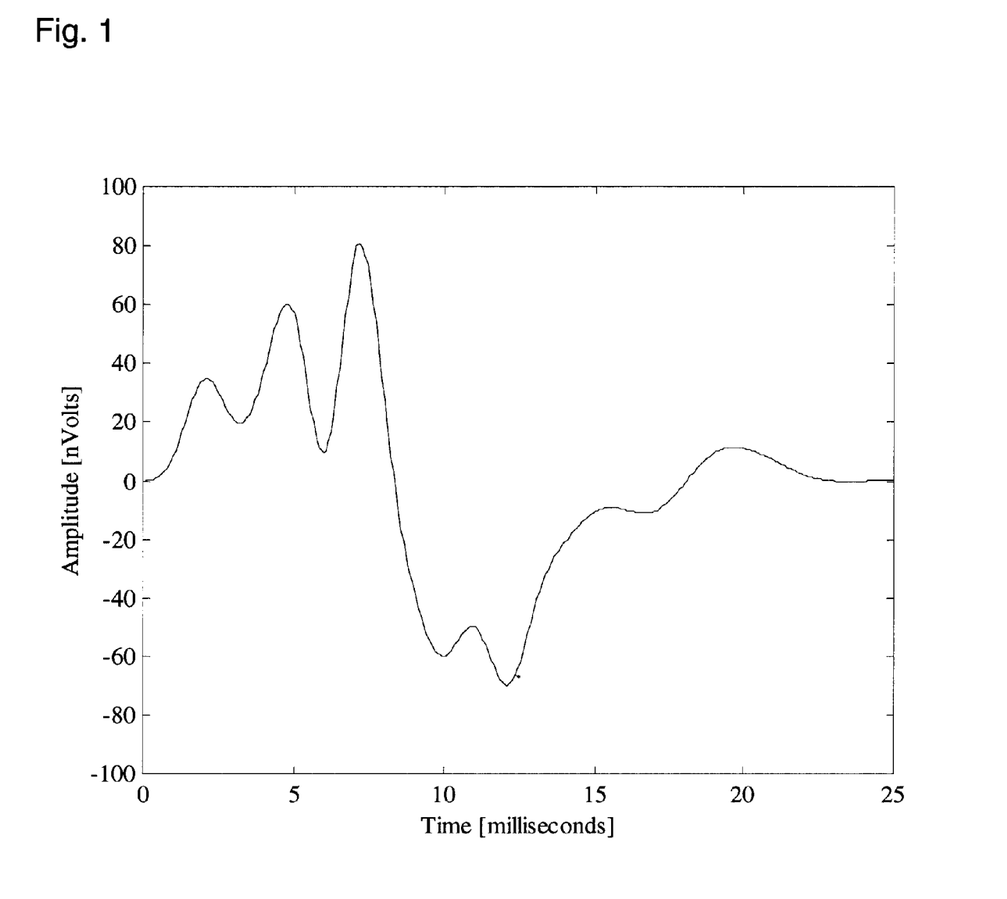
FIG. 1 illustrates a typical ABR waveform.
Figure 2:
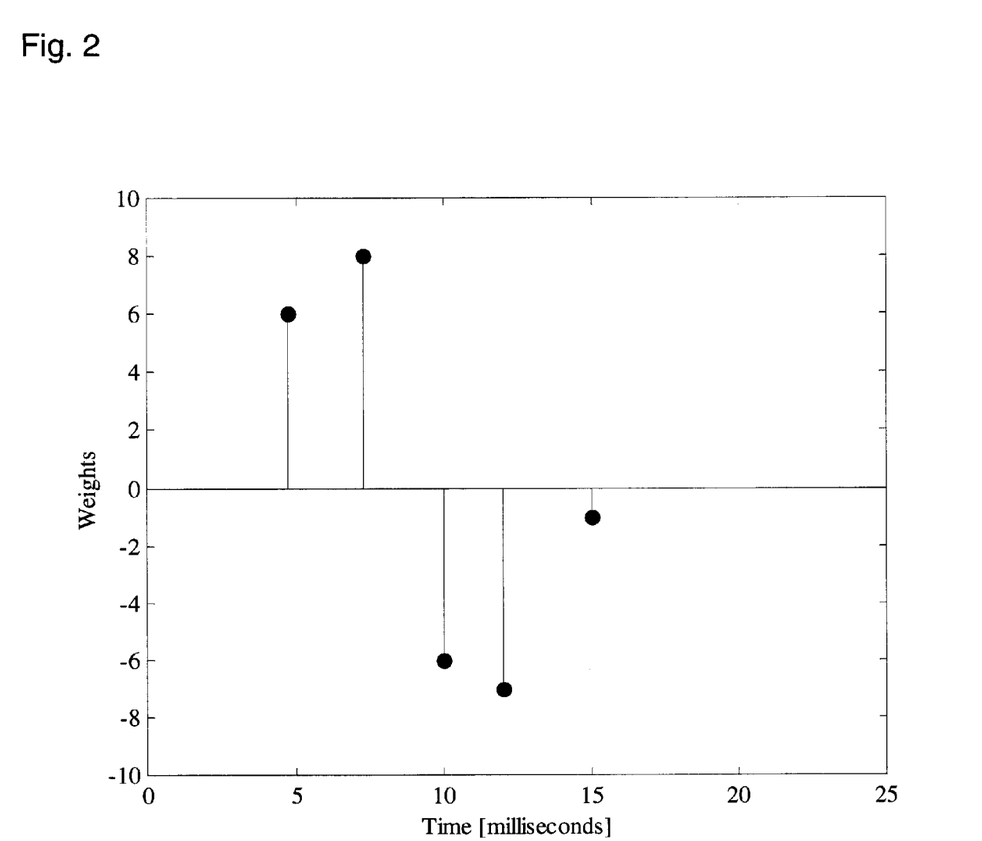
FIG. 2 illustrates a weighted ABR template.

The summed polarity sequence X is then compared with a template waveform, which has been compiled with the use of normative data (FIG. 1). It will be necessary to use different template ABR waveforms for different subject populations and for different hardware configurations. The template waveform is comprised of M weighted points, strategically placed to match the typical ABR waveform. At each of the M points, a template weight $w_m$ is assigned, reflecting the importance and polarity of the given measurement point in ascertaining the presence of an ABR, as derived from normative data. (See FIG. 2). The importance of each measurement point is a function of its amplitude. For any given point m, the sum of the polarities would be $x_m$. The sum of the template weights equals zero.

The present invention uses a test statistic z to aid in determining if an ABR is present. This test statistic is defined as:

$$z = \frac{\sum_{m=1} w_m(x_m - \mu_x)}{\sqrt{Npq \sum_{m=1}^{M} w_m^2}}$$

where p is the probability of positive polarity, and q is the complementary probability. The test statistic z scores the random binary array X by multiplying its elements $x_m$ at each template point m with the corresponding weight $w_m$, and summing these results into a single, normalized number. Now, in the absence of an ABR, the peak of the distribution of z would remain at zero, while in the presence of an ABR, the test statistic would grow with increasing number of sweeps.

Subjects exhibit variability in the latency of the ABR waveform, so that different subjects, each of whom can hear, may exhibit ABR waveforms at different times after the click stimulus. In order to compensate for this variability, the test statistic z may be recalculated at various times. The highest z from each of these time-shifted samples, $z_{max}$, can be saved and used to determine the presence of the ABR. In a preferred embodiment of the present invention, a "Pass" is indicated when $z_{max}$ reaches a value that is 4 standard deviations from zero.

Additionally, it has been found that the peak-to-peak amplitude of the ABR in normal-hearing babies varies from baby to baby. As noted above, the present invention accounts for this variability in ABR amplitude, by making conservative assumptions about the ABR amplitude of the subject, who is being tested. Therefore, as described above, the allowable maximum variance, $\sigma_{min}^2$, and the allowable maximum signal energy, $E_{min}$, are calculated by reference to normative data pertaining to the $5^{th}$ percentile ABR waveform ($\sigma_{min}^2 = 1.7 \times 10^{-11}$ Volts$^2$) based on an analysis with normative data.

The generation of the click stimulus, the detection, processing and analysis of the EEG response signal, the detection, processing and analysis of acoustic noise, and the display of the results are performed by conventional electronic means, e.g., digital microprocessor controlled devices. Such devices include a transducer to generate the auditory stimulus, conventional electrodes to detect the EEG response signal, and a conventional microphone to detect the acoustic noise. To analyze the EEG response signal and the acoustic noise signal, a processing unit, such a conventional microprocessor, and memory unit are needed. Additionally, a display unit and optionally an input device, such as a mouse and/or a keyboard, provide operator interface.

As shown in FIG. 3, stimulus generator 10 generates the click stimulus, and EEG transducer 20 detects the EEG response to the stimulus. Next, EEG signal conditioning 30 and signal processing 40 occur, readying the EEG response for analysis. Analysis of EEG signal weight 60 follows in accordance with the present invention, after which statistical analysis for the presence of an ABR 50 occurs. Also during evaluation, microphone 80 detects acoustic noise, and this acoustic signal undergoes signal conditioning 90 and processing 100, and analysis of acoustic noise weight 110 follows, in accordance with the present invention. Normative data 70 is used for both types of weight analysis. Finally, a control device with user interface 120 displays the results.

Although it is not the preferred embodiment, the present invention could also be practiced by relative weighting, that is, by weighting polarity sequences $X_c$ or $X_n$ based on the amount of EEG and/or acoustic noise in comparison to the amount of such noise in other responses from the same test.

One skilled in the art will appreciate that the present invention can be practiced by other than the preferred embodiments, which are presented for purposes of illustration and not of limitation. For example, different parameters of noise characterization in the amplitude, time and/or frequency domain, or different weighting functions can be used with the present invention. In addition, the specific parameter values identified are useful or representative parameter values, and other values or ranges of values for these parameters may be used without departing from the spirit and scope of the invention.

We claim:

1. A device for hearing evaluation of a subject comprising:
   means for repeatedly delivering an auditory stimulus;
   means for sampling electroencephalographic (EEG) responses to said stimulus;
   means for measuring EEG noise amounts associated with said EEG responses;
   means for weighting said EEG responses based on the continuous relationship of said EEG noise amounts to normative data; and
   means for determining that the Auditory Brainstem Response ("ABR") waveform is present, using said weighted EEG responses.

2. The device according to claim 1, wherein said means for measuring the EEG noise amounts comprises means to measure and compute composite signal noise variances in said EEG responses.

3. The device according to claim 1 or 2, wherein said means for weighting said EEG responses comprises means to calculate the ratio between said EEG noise amounts and a predetermined EEG noise level calculated using normative data.

4. The device according to claim 3, wherein said means for weighting said EEG responses assigns a value between 0 and 1 to said EEG responses.

5. A device for hearing evaluation of a subject comprising:
   means for repeatedly delivering an auditory stimulus;
   means for sampling EEG responses to said stimulus;
   means for sampling acoustic noise amounts associated with said EEG responses;
   means for weighting said EEG responses based on the relationship of said acoustic noise amounts to normative data; and
   means for determining that the ABR waveform is present, using said weighted EEG responses.

6. The device according to claim 5, wherein said means for sampling acoustic noise amounts comprises means for measuring acoustic noise, and means for computing a composite signal energy associated with acoustic noise.

7. The device according to claim 6, wherein said composite signal energy is computed with reference to acoustic noise sampled both before and during the time that the auditory stimulus is delivered.

8. The device according to claim 5 or 7, wherein said means for weighting said EEG responses comprises means to calculate the ratio between said acoustic noise amounts and a predetermined acoustic noise level calculated using normative data.

9. The device according to claim 8, wherein said means for weighting said EEG responses assigns a value between 0 and 1 to said EEG responses.

10. A device for hearing evaluation of a subject comprising:
    means for repeatedly delivering an auditory stimulus;

means for sampling EEG responses to said stimulus;

means for measuring EEG noise amounts associated with said EEG responses;

means for sampling acoustic noise amounts associated with said EEG responses;

means for weighting said EEG responses based on the continuous relationship of said acoustic noise amounts to normative data;

means for further weighting said EEG responses based on the continuous relationship of said EEG noise amounts to normative data; and means for determining that the ABR waveform is present, using said weighted EEG responses.

11. The device according to claim 10, wherein said means for measuring EEG noise amounts comprises means to measure and compute composite signal noise variances in said EEG responses.

12. The device according to claim 10, wherein said means for sampling acoustic noise amounts comprises means for measuring acoustic noise, and means for computing a composite signal energy associated with acoustic noise.

13. The device according to claim 10, 11 or 12, wherein said means for further weighting said EEG responses based on the continuous relationship of said EEG noise amounts to normative data comprises means to calculate the ratio between said EEG noise amounts and a predetermined EEG noise level calculated using normative data.

14. The device according to claim 10, 11 or 12, wherein said means for weighting said EEG responses based on the relationship of said acoustic noise amounts to normative data comprises means to calculate the ratio between said acoustic noise amounts and a predetermined acoustic noise level calculated using normative data.

15. The device according to claim 10, 11 or 12, wherein said means for further weighting said EEG responses based on the continuous relationship of said EEG noise amounts to normative data assigns a value between 0 and 1 to said EEG responses.

16. The device according to claim 10, 11 or 12, wherein said means for weighting said EEG responses based on the relationship of said acoustic noise amounts to normative data assigns a value between 0 and 1 to said EEG responses.

17. A method for hearing evaluation of a subject which comprises the steps of:

repeatedly delivering an auditory stimulus;

sampling EEG responses to said stimulus;

measuring EEG noise amounts associated with said EEG responses;

weighting said EEG responses based on the continuous relationship of said EEG noise amounts to normative data; and determining that the ABR waveform is present, using said weighted EEG responses.

18. A method for hearing evaluation of a subject which comprises the steps of:

repeatedly delivering an auditory stimulus;

sampling EEG responses to said stimulus;

sampling acoustic noise amounts associated with said EEG responses;

weighting said EEG responses based on the relationship of said acoustic noise amounts to normative data; and determining that the ABR waveform is present, using said weighted EEG responses.

19. A method for hearing evaluation of a subject which comprises the steps of:

repeatedly delivering an auditory stimulus;

sampling EEG responses to said stimulus;

measuring EEG noise amounts associated with said EEG responses;

sampling acoustic noise amounts associated with said EEG responses;

weighting said EEG responses based on the relationship of said acoustic noise amounts to normative data;

further weighting said EEG responses based on the continuous relationship of said EEG noise amounts to normative data; and determining that the ABR waveform is present, using said weighted EEG responses.

20. A system for hearing evaluation of a subject, comprising:

a transducer having an audible click output stimulus;

an electrode system adapted to detect an EEG response to said stimulus;

a processor, responsive to said EEG response, having
means for sampling EEG responses;
means for processing the sampled EEG responses and identifying therein a EEG noise component;
means for weighting said EEG responses based on the continuous relationship of said EEG noise amounts to normative data; and
means for determining that the an ABR is present, based on said weighted EEG responses.

21. A system for hearing evaluation of a subject, comprising:

a transducer having an audible click output stimulus;

an electrode system adapted to detect an EEG response to said stimulus;

a processor, responsive to said EEG response, having
means for sampling EEG responses;
means for sampling acoustic noise amounts associated with said EEG responses;
means for weighting said EEG responses based on the relationship of said acoustic noise amounts to normative data; and
means for determining that the ABR waveform is present, using said weighted EEG responses.

22. A device for hearing evaluation of a subject comprising:

means for repeatedly delivering an auditory stimulus;

means for measuring EEG responses to the stimulus, said responses having polarities at each point in time;

means for sampling EEG responses to said stimulus;

means for digitizing said EEG responses;

means for transforming said digitized EEG responses into a series of binary numbers corresponding to the polarities of said EEG responses;

means for transforming said binary numbers into an array of polarity sums;

means for measuring EEG noise amounts associated with said EEG responses;

means for weighting said array of polarity sums based on said EEG noise amounts; and means for determining the probability of the presence of an ABR waveform, using said weighted array of polarity sums.

23. The device according to claim 22, wherein said means for weighting comprises means for weighting said array of polarity sums based on the continuous relationship of said EEG noise amounts to normative data.

24. The device according to claim 23, wherein said means for measuring EEG noise amounts associated with said EEG responses comprises means to measure and compute composite signal noise variances in said EEG responses.

25. The device according to claim 23 or 24, wherein said means for weighting said array of polarity sums comprises means to calculate the ratio between said EEG noise amounts and a predetermined EEG noise level calculated using normative data.

26. The device according to claim 25, wherein said means for weighting said array of polarity sums assigns a weight between 0 and 1 to said array of polarity sums.

27. A device for hearing evaluation of a subject comprising:
   means for repeatedly delivering an auditory stimulus;
   means for measuring EEG responses to the stimulus, said responses having polarities at each point in time;
   means for sampling EEG responses to said stimulus;
   means for digitizing said EEG responses;
   means for transforming said digitized EEG responses into a series of binary numbers corresponding to the polarities of said EEG responses;
   means for transforming said binary numbers into an array of polarity sums;
   means for measuring acoustic noise amounts associated with said EEG responses;
   means for weighting said array of polarity sums based on said acoustic noise amounts; and
   means for determining the probability of the presence of an ABR waveform, using said weighted array of polarity sums.

28. The device according to claim 27, wherein said means for weighting comprises means for weighting said array of polarity sums based on the relationship of said acoustic noise amounts to normative data.

29. The device according to claim 28, wherein said means for measuring acoustic noise amounts comprises means for measuring acoustic noise, and means for computing a composite signal energy associated with acoustic noise.

30. The device according to claim 28, wherein said composite signal energy is computed with reference to acoustic noise sampled both before and during the time that the auditory stimulus is delivered.

31. The device according to claim 27 or 29, wherein said means for weighting said array of polarity sums comprises means to calculate the ratio between said acoustic noise amounts and a predetermined acoustic noise level calculated using normative data.

32. The device according to claim 31, wherein said means for weighting said array of polarity sums assigns a weight between 0 and 1 to said array of polarity sums.

33. A device for hearing evaluation of a subject comprising:
   means for repeatedly delivering an auditory stimulus;
   means for measuring EEG responses to the stimulus, said responses having polarities at each point in time;
   means for sampling EEG responses to said stimulus;
   means for digitizing said EEG responses;
   means for transforming said digitized EEG responses into a series of binary numbers corresponding to the polarities of said EEG responses;
   means for transforming said binary numbers into an array of polarity sums;
   means for measuring EEG noise amounts associated with said EEG responses;
   means for sampling acoustic noise amounts associated with said EEG responses;
   means for weighting said array of polarity sums based on said acoustic noise amounts;
   means for further weighting said array of polarity sums based on said EEG noise amounts; and
   means for determining the probability of the presence of an ABR waveform, using said weighted array of polarity sums.

34. The device according to claim 33, wherein
   said means for weighting said array of polarity sums based on said acoustic noise amounts comprises means for weighting said array of polarity sums based on the relationship of said acoustic noise amounts to normative data; and
   said means for further weighting said array of polarity sums based on said EEG noise amounts comprises means for weighting said array of polarity sums based on the continuous relationship of said EEG noise amounts to normative data.

35. The device according to claim 34, wherein said means for measuring EEG noise amounts comprises means to measure and compute composite signal noise variances in said EEG responses.

36. The device according to claim 34, wherein said means for sampling acoustic noise amounts comprises means for measuring acoustic noise, and means for computing a composite signal energy associated with acoustic noise.

37. The device according to claim 34, 35, or 36, wherein said means for weighting said array of polarity sums comprises means to calculate the ratio between said EEG noise amounts and a predetermined EEG noise level calculated using normative data.

38. The device according to claim 34, 35, or 36 wherein said means for weighting said array of polarity sums comprises means to calculate the ratio between said acoustic noise amounts and a predetermined acoustic noise level calculated using normative data.

39. The device according to claim 34, 35, or 36, wherein said means for further weighting said array of polarity sums based on the continuous relationship of said EEG noise amounts to normative data assigns a value between 0 and 1 to said array of polarity sums.

40. The device according to claim 34, 35, or 36, wherein said means for weighting said array of polarity sums based on the relationship of said acoustic noise amounts to normative data assigns a value between 0 and 1 to said array of polarity sums.

41. A method for hearing evaluation of a subject which comprises the steps of
   repeatedly delivering an auditory stimulus to a subject;
   measuring EEG responses to the stimulus, said responses having polarities at each point in time;
   digitizing said EEG responses;
   transforming said digitized EEG responses into a series of binary numbers corresponding to the polarities of said EEG responses;
   transforming said binary numbers into an array of polarity sums; measuring EEG noise amounts associated with said EEG digitized responses;
   weighting said array of polarity sums based on the continuous relationship of said EEG noise amounts to normative data; and;
   determining the probability of the presence of an ABR waveform, using said weighted EEG responses.

42. A method for hearing evaluation of a subject which comprises the steps of
   repeatedly delivering an auditory stimulus to a subject;
   measuring EEG responses to the stimulus said response having a polarity at each point in time;
   digitizing said EEG responses;
   transforming said digitized EEG responses into a series of binary numbers corresponding to the polarity of said EEG responses;
   transforming said binary numbers into an array of polarity sums;
   sampling acoustic noise amounts associated with said digitized EEG responses;
   weighting said array of polarity sums based on the relationship of said acoustic noise amounts to normative data; and
   determining the probability of the presence of an ABR waveform, using said weighted array of polarity sums.

43. A method for hearing evaluation of a subject which comprises the steps of:
   repeatedly delivering an auditory stimulus to a subject;
   measuring EEG responses to the stimulus said response having a polarity at each point in time;
   digitizing said EEG responses;
   transforming said digitized EEG responses into a series of binary numbers corresponding to the polarity of said EEG responses;
   transforming said binary numbers into an array of polarity sums;
   measuring EEG noise amounts associated with said digitized EEG responses;
   sampling acoustic noise amounts associated with said digitized EEG responses;
   weighting said array of polarity sums based on the relationship of said acoustic noise amounts to normative data;
   further weighting said array of polarity sums based on the continuous relationship of said EEG noise amounts to normative data; and
   determining the probability of the presence of an ABR waveform, using said weighted array of polarity sums.

44. A system for hearing evaluation of a subject, comprising:
   a transducer having an audible click output stimulus;
   an electrode system adapted to detect an EEG response to said stimulus;
   a processor, responsive to said EEG response, having
      means for repeatedly delivering an auditory stimulus;
      means for measuring EEG responses to the stimulus, said responses having polarities at each point in time;
      means for sampling EEG responses to said stimulus;
      means for digitizing said EEG responses;
      means for transforming said digitized EEG responses into a series of binary numbers corresponding to the polarities of said EEG responses;
      means for transforming said binary numbers into an array of polarity sums;
      means for measuring EEG noise amounts associated with said EEG responses;
      means for weighting said array of polarity sums based on the continuous relationship of said EEG noise amounts to normative data; and
      means for determining the probability of the presence of an ABR, based on said weighted array of polarity sums.

45. A system for hearing evaluation of a subject, comprising:
   a transducer having an audible click output stimulus;
   an electrode system adapted to detect an EEG response to said stimulus;
   a processor, responsive to said EEG response, having
      means for repeatedly delivering an auditory stimulus;
      means for measuring EEG responses to the stimulus, said responses having polarities at each point in time;
      means for sampling acoustic noise amounts associated with said EEG responses;
      means for digitizing said EEG responses;
      means for transforming said digitized EEG responses into a series of binary numbers corresponding to the polarities of said EEG responses;
      means for transforming said binary numbers into an array of polarity sums;
      means for weighting said array of polarity sums based on the relationship of said acoustic noise amounts to normative data; and
      means for determining the probability of the presence of an ABR, based on said weighted array of polarity sums.

* * * * *